United States Patent
Lewerenz et al.

(10) Patent No.: US 12,242,140 B2
(45) Date of Patent: Mar. 4, 2025

(54) LOGARITHMICALLY INCREMENTED MAGNIFIERS FOR LOW VISION REHABILITATION

(71) Applicants: David Charles Lewerenz, Denver, CO (US); Gregory Robert Hopkins, II, Columbus, OH (US)

(72) Inventors: David Charles Lewerenz, Denver, CO (US); Gregory Robert Hopkins, II, Columbus, OH (US)

(*) Notice: Subject to any disclaimer, the term of this patent is extended or adjusted under 35 U.S.C. 154(b) by 100 days.

(21) Appl. No.: 17/412,673

(22) Filed: Aug. 26, 2021

(65) Prior Publication Data

US 2022/0221737 A1 Jul. 14, 2022

Related U.S. Application Data

(60) Provisional application No. 63/070,790, filed on Aug. 26, 2020.

(51) Int. Cl.
*G02C 7/06* (2006.01)
*A61B 3/032* (2006.01)
(Continued)

(52) U.S. Cl.
CPC .............. *G02C 7/061* (2013.01); *A61B 3/032* (2013.01); *G02C 7/022* (2013.01); *G02C 7/028* (2013.01); *G02B 25/02* (2013.01)

(58) Field of Classification Search
CPC .......... G02C 7/027; G02C 7/025; G02C 7/04; G02C 7/061; G02C 7/022; G02C 7/028;
(Continued)

(56) References Cited

U.S. PATENT DOCUMENTS

| 686,616 A | * | 11/1901 | Johnquest | A61B 3/02 |
| | | | | 351/203 |
| 1,802,997 A | * | 4/1931 | Yetta | A61H 5/00 |
| | | | | 351/203 |

(Continued)

FOREIGN PATENT DOCUMENTS

| WO | WO-0102897 A1 * | 1/2001 | .............. A61B 3/028 |
| WO | WO-2004023989 A1 * | 3/2004 | .......... A61B 3/1015 |

*Primary Examiner* — Mustak Choudhury

(57) ABSTRACT

A method is presented that includes providing a set of spectacle magnifiers, each magnifier in the set having a different corresponding diopter value, the magnifiers together providing a sequence of evenly incremented diopter values. The set further includes a magnifier having a lowest value ($MAG_0$), a magnifier having a highest value ($MAG_N$), and one or more magnifiers having values between those of $MAG_0$ and $MAG_N$. In one or more embodiments, the diopter value increment between any two successive magnifiers of the set is equal to K(0.1) log, where K is an integer >0 or a fraction whose denominator is an integer >0. In one or more embodiments, one or more elements of the set are packaged for sale. In some embodiments, a set of optical, telescopic, or electronic magnification devices may be provided, the set including one or more devices configured to provide non-rectilinear magnification.

20 Claims, 13 Drawing Sheets

Non-Rectilinear Magnification using the logMAG Scale

| 0.0 | 0.10 | 0.20 | 0.30 |

(51) Int. Cl.
  *G02C 7/02*  (2006.01)
  *G02B 25/02*  (2006.01)

(58) Field of Classification Search
  CPC ....... G02C 7/088; A61B 3/0025; A61B 3/032; A61F 2/16; G02B 25/02; G02B 25/002; G02B 3/10; G02B 7/02; G02B 23/00; A61H 2201/0188; A61H 5/00
  USPC .......................................... 351/200–203, 228
  See application file for complete search history.

(56) References Cited

U.S. PATENT DOCUMENTS

| | | | | | |
|---|---|---|---|---|---|
| 2,149,897 | A | * | 3/1939 | Ogle | A61B 3/04 351/201 |
| 2,183,028 | A | * | 12/1939 | Ogle | A61B 3/04 351/201 |
| 3,875,934 | A | * | 4/1975 | Sadanaga | A61H 5/00 351/203 |
| 5,028,127 | A | * | 7/1991 | Spitzberg | G02B 7/002 351/158 |
| 5,220,361 | A | * | 6/1993 | Lehmer | G06V 40/19 351/224 |
| 7,528,882 | B2 | * | 5/2009 | Saori | G02B 13/22 348/335 |
| 2003/0164923 | A1 | * | 9/2003 | Hirohara | A61B 3/06 351/216 |
| 2008/0143960 | A1 | * | 6/2008 | MacRae | A61B 3/04 351/230 |
| 2008/0291395 | A1 | * | 11/2008 | Dai | G02C 7/041 351/205 |
| 2010/0134757 | A1 | * | 6/2010 | Arcona | A61H 5/00 351/203 |
| 2014/0211166 | A1 | * | 7/2014 | Scherlen | A61B 3/02 351/239 |
| 2015/0062536 | A1 | * | 3/2015 | Auger | A61B 3/0025 351/239 |

\* cited by examiner

Figure 1
| Equivalent Power | Log₁₀ of Equivalent Power | Diagram of Proximal Magnification |
|---|---|---|
| +5.0 D | 0.7 | 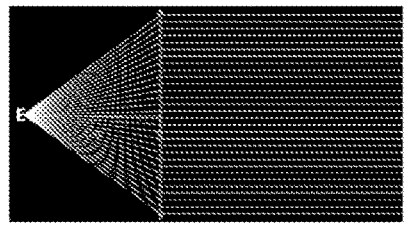 |
| +6.3 D | 0.8 | 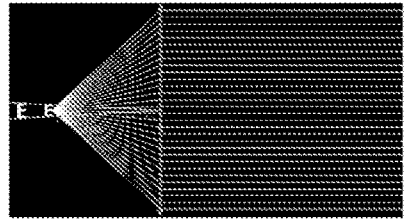 |
| +8.0 D | 0.9 | 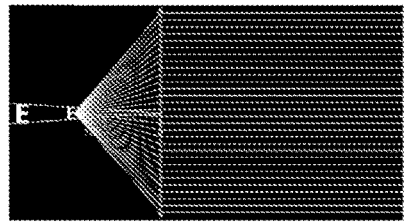 |
| +10.0 D | 1.0 | 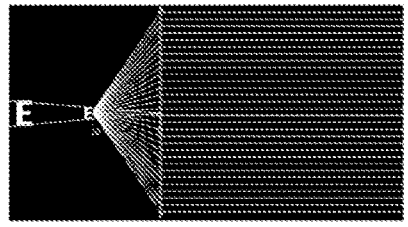 |
| +12.5 D | 1.1 | 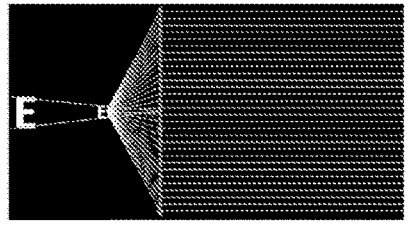 |

Figure 1, Continued
| | | |
|---|---|---|
| +16.0 D | 1.2 | 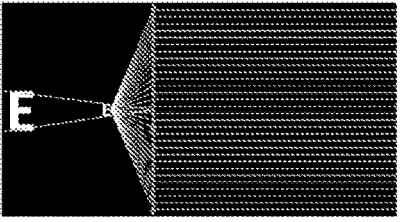 |
| +20.0 D | 1.3 | 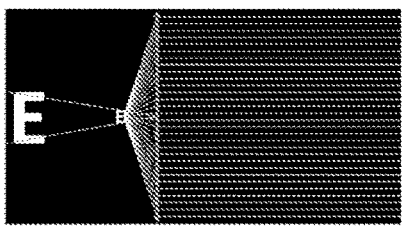 |
| +25.0 D | 1.4 | 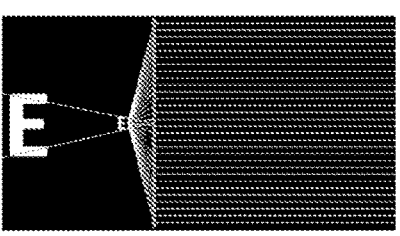 |
| +32.0 D | 1.5 | 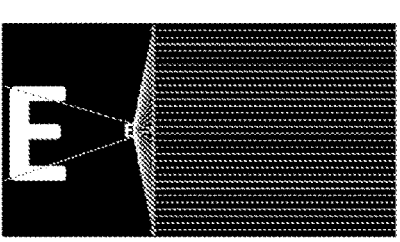 |
| +40.0 D | 1.6 | 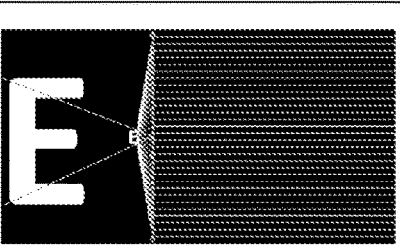 |
| +50.0 D | 1.7 | 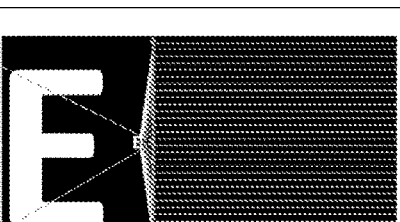 |

Figure 2A

| Enlargement Ratio | Log$_{10}$ of Enlargement Ratio | Image Distance | Diagram of Transverse Optical Magnification |
|---|---|---|---|
| 1.6X | 0.2 | 12 cm | |
| 2.0X | 0.3 | 16 cm | |
| 2.5X | 0.4 | 19 cm | |
| 3.2X | 0.5 | 22 cm | |
| 4.0X | 0.6 | 23 cm | |

Figure 2A, Continued
| | | | |
|---|---|---|---|
| 5.0X | 0.7 | 25 cm | 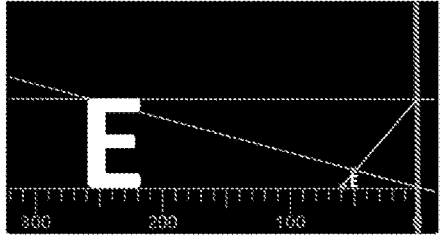 |
| 6.3X | 0.8 | 27 cm | 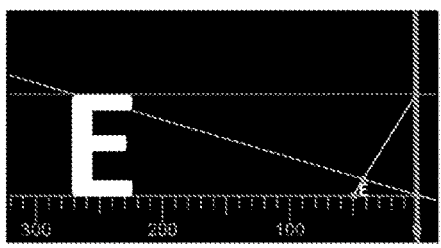 |
| 8.0X | 0.9 | 28 cm | 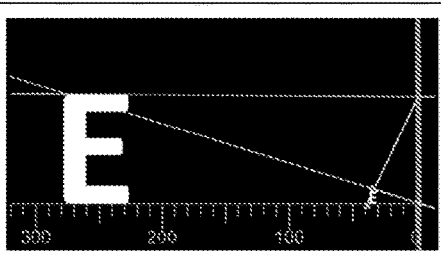 |
| 10.0X | 1.0 | 28 cm | 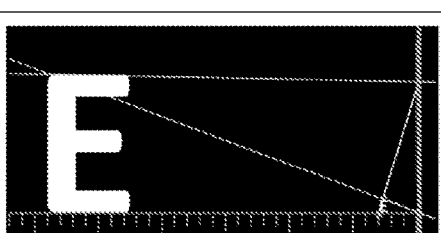 |
| 12.5X | 1.1 | 29 cm | 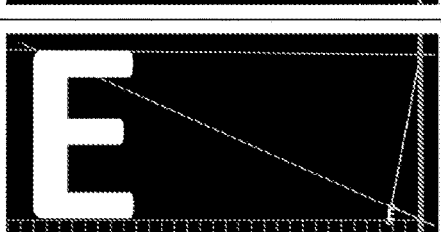 |
| 16.0X | 1.2 | 30 cm |  |

Figure 3A – Examples of Magnification Devices
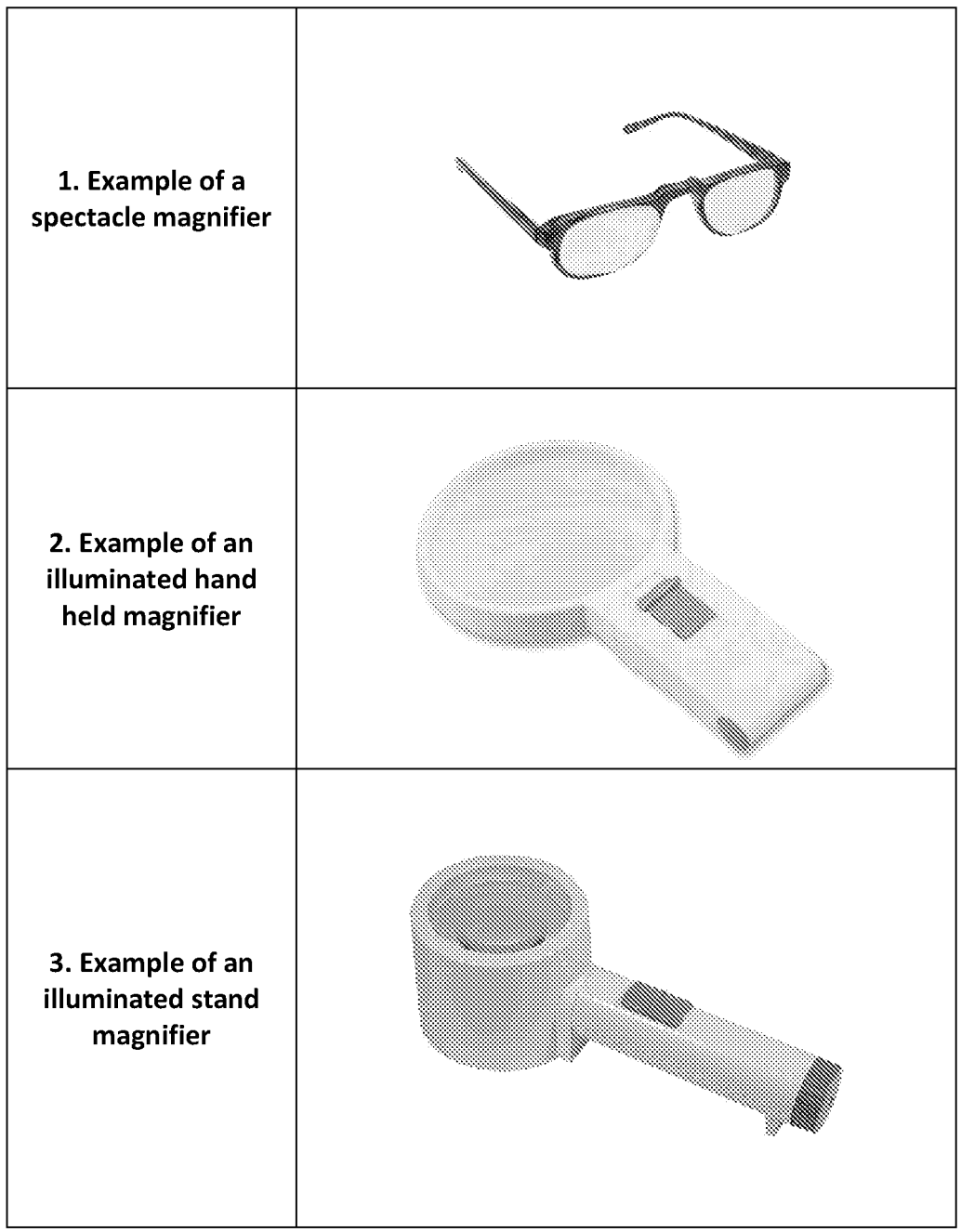

Figure 3A, Continued
| | |
|---|---|
| 4. Example of a set of illuminated hand held and stand magnifiers | 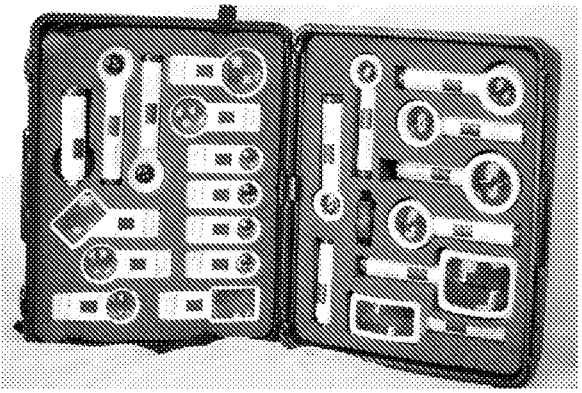 |
| 5. Example of telescopic magnifiers, which could be monocular, binocular, handheld, or spectacle mounted |  |
| 6. Example of electronic magnifiers that could be programed to follow logMAG progression | 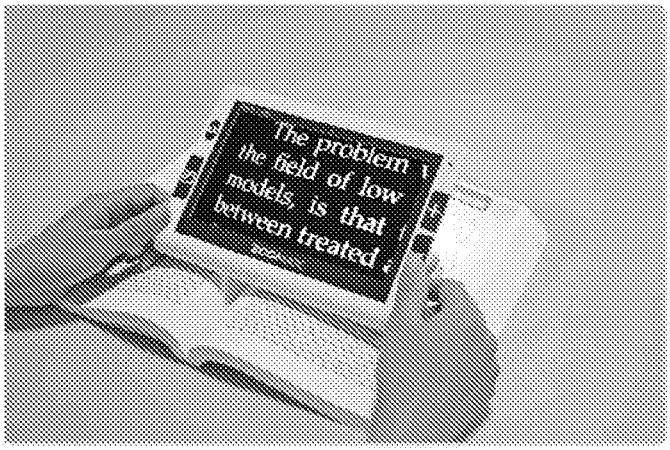 |

Figure 3B – Electronic Magnifier (Larger Image)

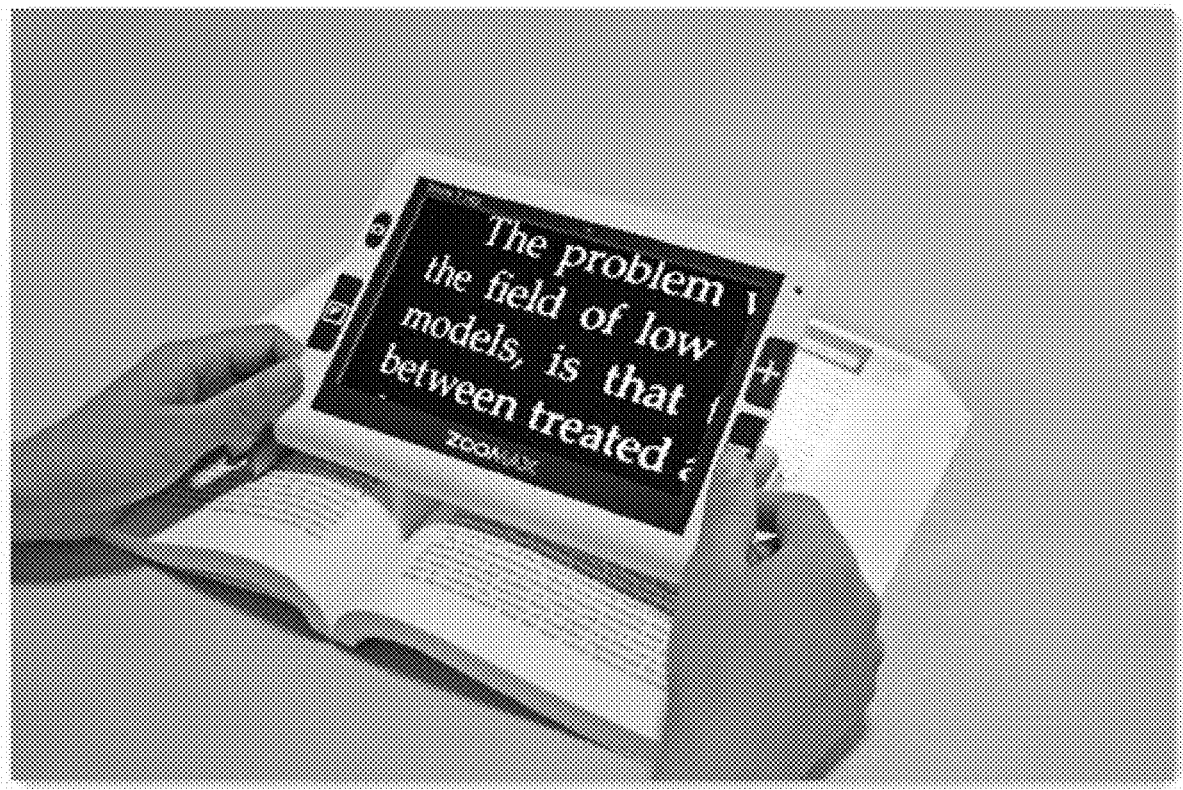

Figure 3C – Non-Rectilinear Magnification using the logMAG Scale

| abore et dolore m inim veniam, llamco laboris ni consequat. Duis rit in voluptate v iat nulla pariatur. idatat non pro | ut labore et dolore mag minim veniam, qu ullamco laboris nisi do consequat. Duis au derit in voluptate velit fugiat nulla pariatur. Ex cupidatat non proide | nt ut labore et dolore magna d minim veniam, quis ion ullamco laboris nisi ut modo consequat. Duis aute enderit in voluptate velit e u fugiat nulla pariatur. Exce t cupidatat non proident | idunt ut labore et dolore magna ali ad minim veniam, quis n itation ullamco laboris nisi ut ali ommodo consequat. Duis aute iru prehenderit in voluptate velit esse re eu fugiat nulla pariatur. Excepte ecat cupidatat non proident, s |
|---|---|---|---|
| 0.0 | 0.10 | 0.20 | 0.30 |

Figure 4A – Example Company A Stand Magnifier Specifications
| Indicated Power | Actual Measured Enlargement Ratio | $Log_{10}$ of Enlargement Ratio | Image Distance |
|---|---|---|---|
| 3X | 1.8X | 0.26 | 15 cm |
| 3X | 1.7X | 0.23 | 14 cm |
| 4X | 2.9X | 0.46 | 17 cm |
| 5X | 2.9X | 0.46 | 14 cm |
| 6X | 4.0X | 0.60 | 17 cm |
| 7X | 8.4X | 0.92 | 34 cm |
| 8X | 10.2X | 1.01 | 37 cm |
| 10X | 6.4X | 0.81 | 18 cm |
| 12X | 14.7X | 1.17 | 34 cm |
| 14X | 12.2X | 1.09 | 22 cm |
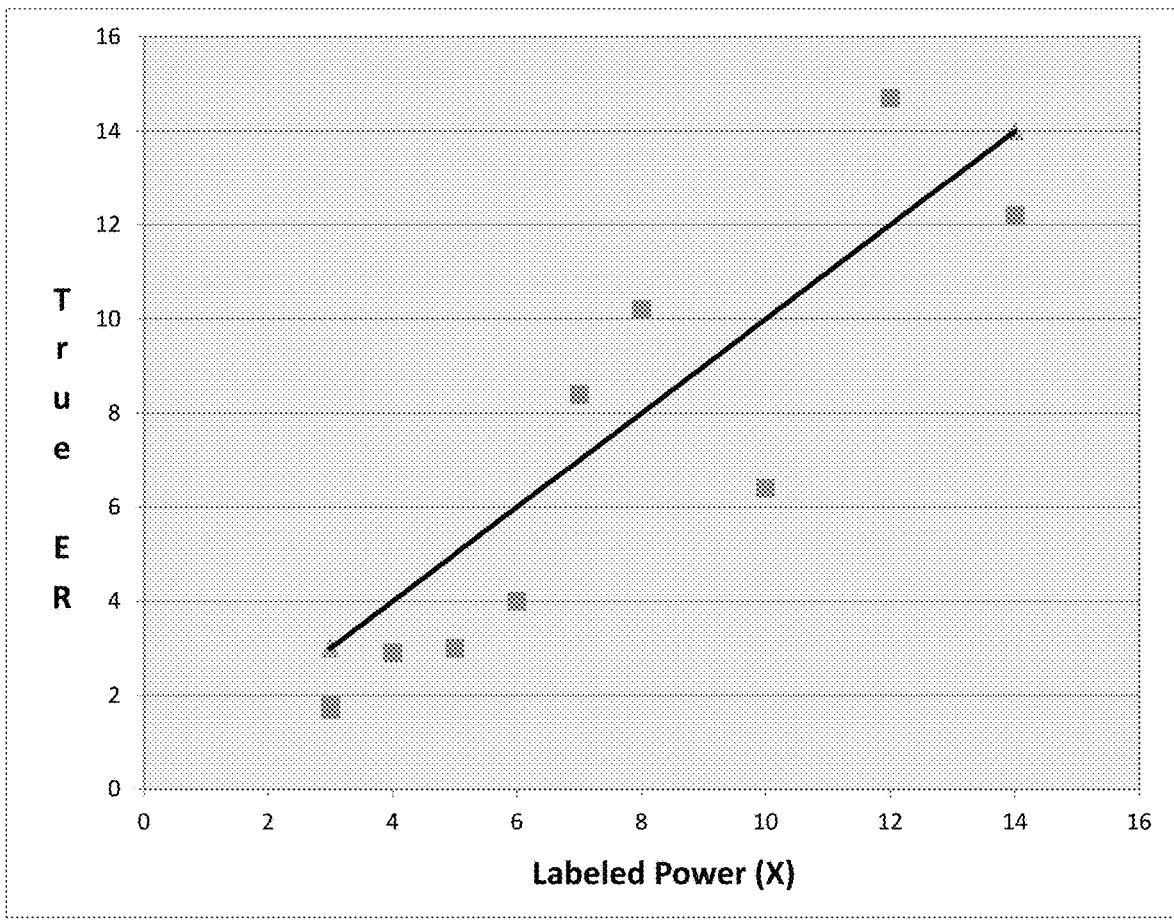

Figure 4B – Example Company B Stand Magnifier Specifications
| Indicated Power | Actual Measured Enlargement Ratio | Log$_{10}$ of Enlargement Ratio | Image Distance |
|---|---|---|---|
| 3X | 2.2X | 0.34 | 21 cm |
| 4X | 3.5X | 0.54 | 21 cm |
| 5X | 3.6X | 0.56 | 19 cm |
| 6X | 6.8X | 0.83 | 31 cm |
| 7X | 12.5X | 1.10 | 48 cm |
| 8X | 10.8X | 1.03 | 38 cm |
| 10.75X | 12.8X | 1.11 | 32 cm |
| 13X | 12.5X | 1.10 | 25 cm |
| 15X | 16.0X | 1.20 | 30 cm |
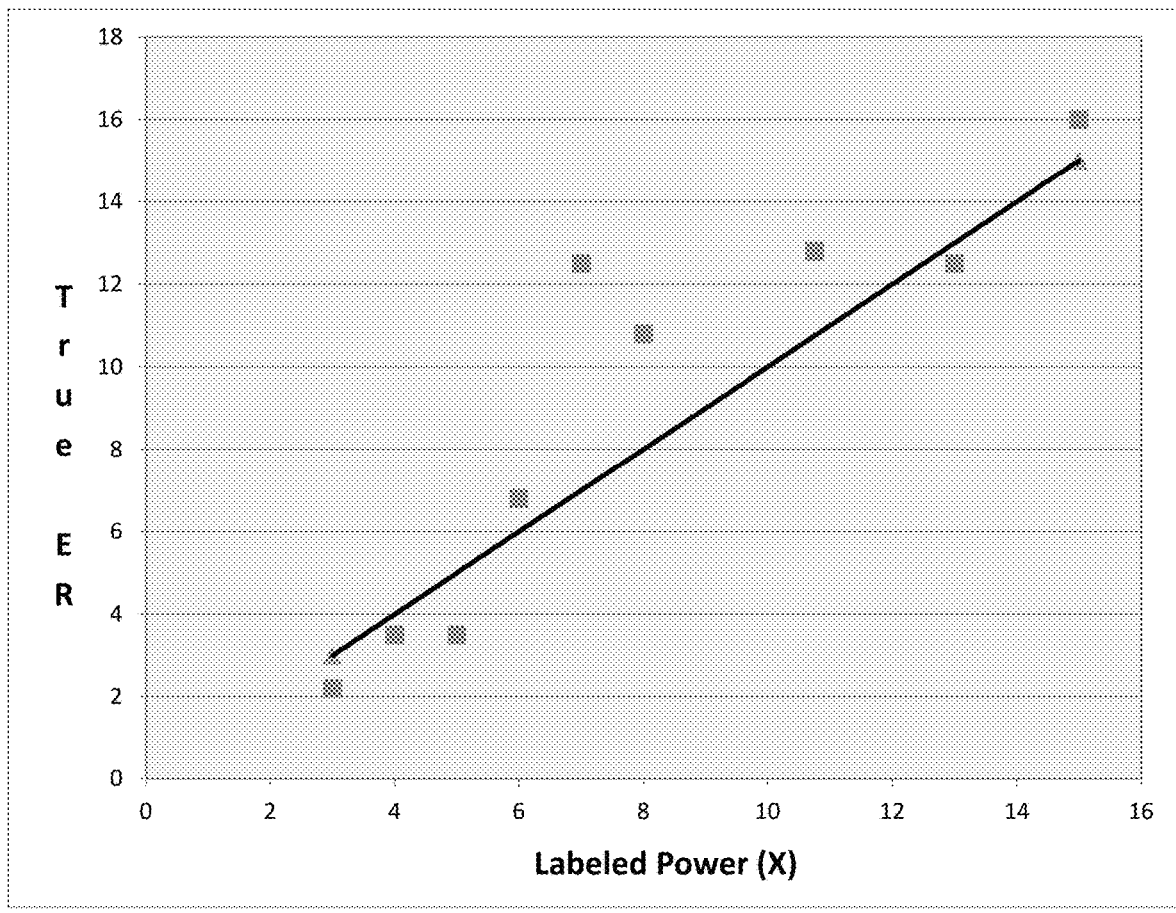

Figure 4C – Example Company C Stand Magnifier Specifications
| Indicated Power | Actual Measured Enlargement Ratio | Log$_{10}$ of Enlargement Ratio | Image Distance |
|---|---|---|---|
| 3X | 3.1X | 0.49 | 15 cm |
| 3.9X | 2.7X | 0.43 | 20 cm |
| 4X | 4.7X | 0.67 | 25 cm |
| 5X | 5.9X | 0.77 | 26 cm |
| 6X | 7.8X | 0.89 | 30 cm |
| 7X | 10.0X | 1.00 | 34 cm |
| 10X | 12.4X | 1.09 | 36 cm |
| 12.5X | 18.3X | 1.26 | 36 cm |
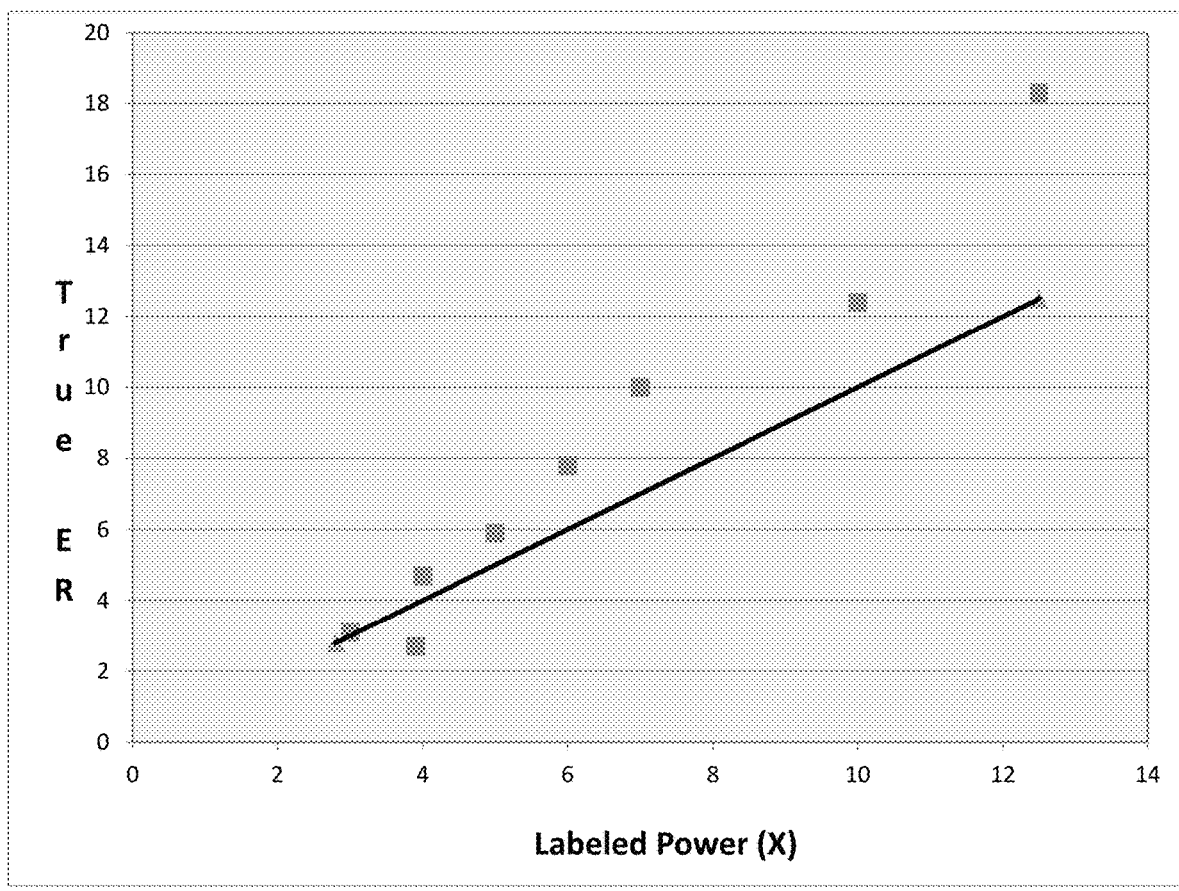

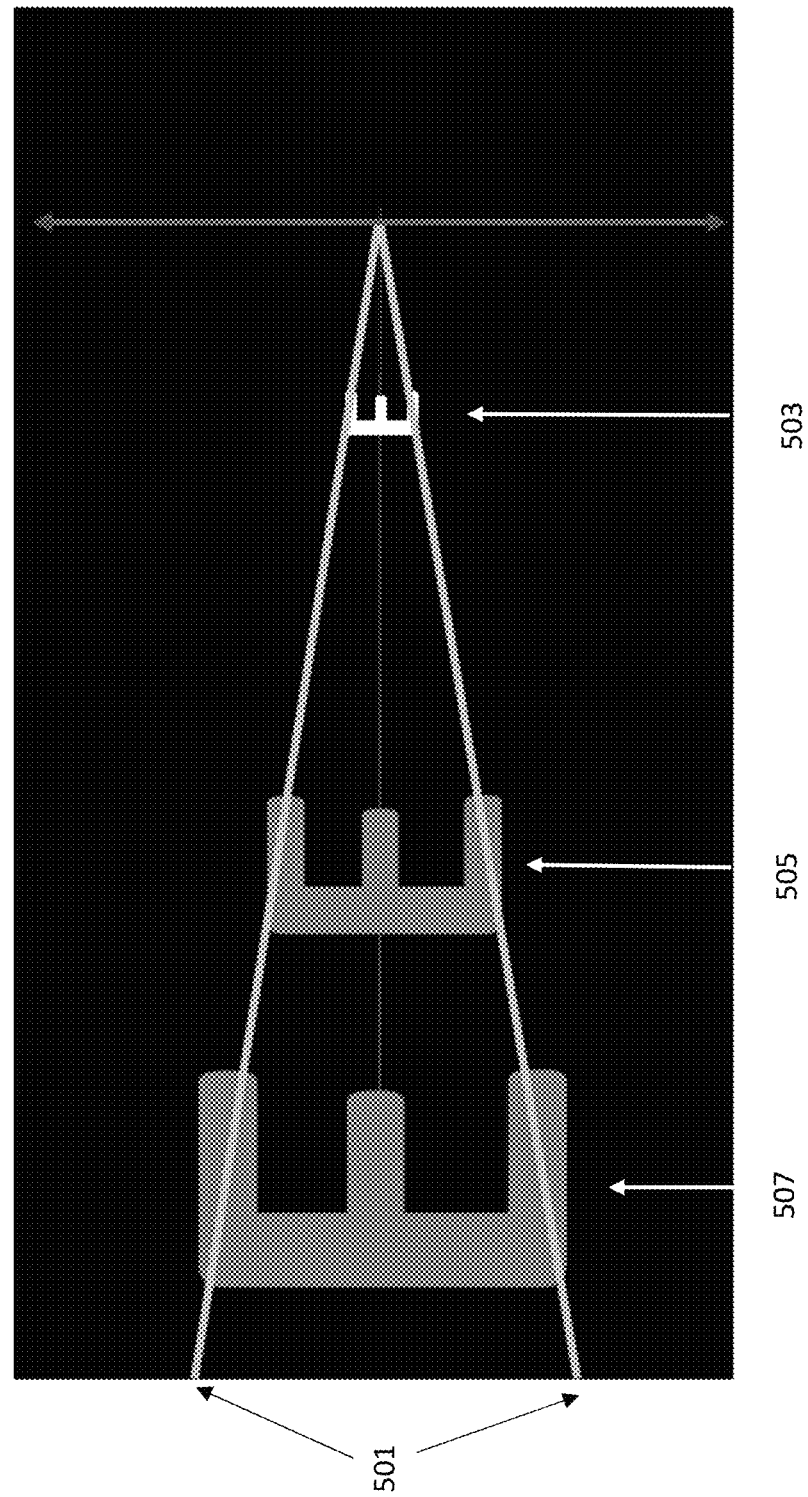

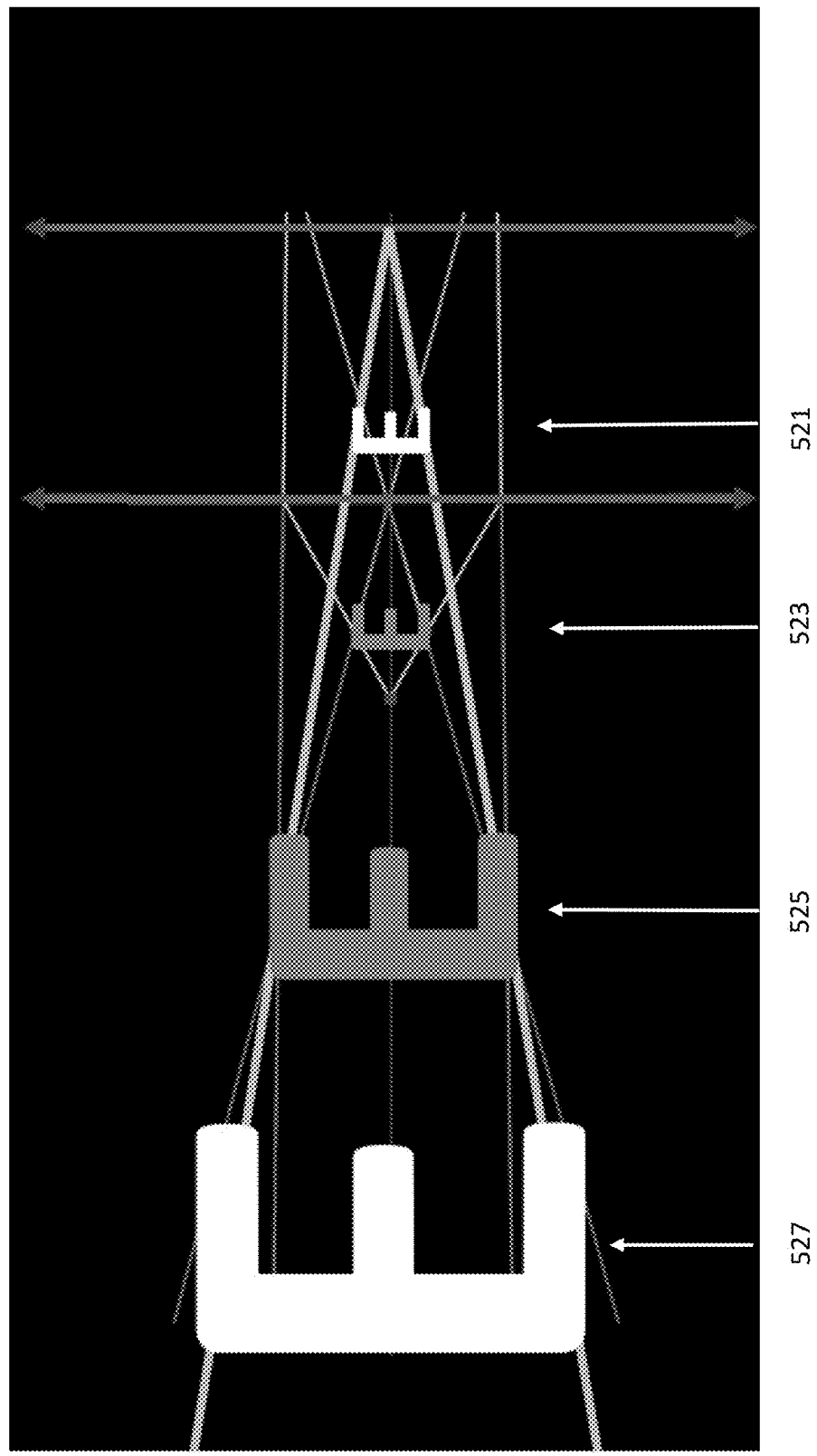

LOGARITHMICALLY INCREMENTED MAGNIFIERS FOR LOW VISION REHABILITATION

CROSS-REFERENCE TO RELATED APPLICATIONS

This application claims the benefit of U.S. Provisional Patent Application No. 63/070,790, filed on Aug. 26, 2020, the disclosure of which is hereby incorporated herein by reference.

BACKGROUND

The present invention relates to low vision rehabilitation, and, in particular, to sets of hand and stand magnifiers that have a progression in logarithmic increments.

Low vision rehabilitation is a medical specialty strongly supported by the National Institutes of Health (NIH), the American Academy of Ophthalmology, the American Academy of Optometry, the American Optometric Association, as well as the World Health Organization (WHO). Low vision rehabilitation seeks to assist people with permanent visual impairment, and thereby enable them to lead independent lives. There are many facets of this specialty, including orientation and mobility specialists, vision rehabilitation therapists, low vision therapists, occupational therapists, social workers, ophthalmologists and optometrists. "Low vision" means that a patient's eyesight is not correctable to normal levels with eyeglasses, surgery or other medical means. These patients may have difficulty achieving their goals and living independently. For many with low vision, magnification is necessary for them to adequately see everyday items.

A mainstay of low vision rehabilitation is magnification, which can take many forms. These may include strong reading glasses, hand and stand magnifiers, telescopes, tele microscopes (optical instruments that combine the functions of a telescope and microscope, e.g., projecting a microscope image onto a screen) and electronic magnification. In the hands of a trained and experienced optometrist or ophthalmologist, prescribing the correct type of device and the correct level of magnification can be done in a systematic and accurate way. However, it is too often the case that magnifiers are provided by untrained personnel, or are chosen by the visually impaired person themselves in a retail context without professional guidance.

Of these forms of magnification, hand and stand magnifiers are commonly used, nearly always with self-contained LED illumination. Unfortunately, the manufacturing of these devices has not followed a rational design and, to further complicate prescribing, they are not accurately labeled. The commonly used "×" power on the label really means nothing in products purchased in a store, and is almost as meaningless when purchased from professional sources.

It is useful to provide solutions to these problems of magnifiers, especially in the context of low vision rehabilitation.

SUMMARY

This Summary is provided to introduce in a simplified form a selection of concepts that are further described below in the Detailed Description. This Summary is not intended to identify key features or essential features of the claimed subject matter, nor is it intended to limit the scope of the claimed subject matter.

According to one embodiment of the present disclosure, a method is provided. The method includes providing a set of spectacle magnifiers, each magnifier having a different corresponding diopter value, the spectacle magnifiers having a sequence of evenly incremented diopter values. The method further includes providing a magnifier having a lowest value ($MAG_0$), providing a magnifier having a highest value ($MAG_N$), and providing one or more magnifiers having values between those of $MAG_0$ and $MAG_N$. In one or more embodiments, the diopter value increment between any two successive spectacle magnifiers of the set is equal to $K(0.1)$ log, where K is an integer >0 or a fraction whose denominator is an integer >0.

In one or more embodiments, one or more spectacle magnifiers of the set may be packaged and sold.

According to a second embodiment of the present disclosure, a set of hand held magnifiers is provided. The set of magnifiers includes three or more magnifiers, each magnifier having a different corresponding diopter value, the magnifiers in the set having a sequence of evenly incremented diopter values. Additionally, the set includes a magnifier having a lowest value ($MAG_0$), a magnifier having a highest value ($MAG_N$), and one or more magnifiers having in between values, wherein the diopter value increment between any two successive magnifiers of the set is equal to $K(0.1)$ log, where K is an integer >0 or a fraction whose denominator is an integer >0.

In one or more embodiments, one or more hand held magnifiers of the set may be packaged and sold.

According to a third embodiment of the present disclosure, a method is provided. The method includes providing a set of stand magnifiers, each magnifier having a different corresponding enlargement ratio, the magnifiers together having a logarithmic progression of powers in enlargement ratio. The method further comprises providing a magnifier having a lowest enlargement ratio value, providing a magnifier having a highest enlargement ratio value and providing one or more magnifiers having in between enlargement ratio values, wherein the enlargement ratio increment between any two successive magnifiers of the set is equal to $K(0.10)$ log, where K is an integer >0 or a fraction whose denominator is an integer >0.

In one or more embodiments, one or more stand magnifiers of the set may be packaged and sold.

According to a fourth embodiment of the present disclosure, a set of telescopes or telemicroscopes is provided. The set includes three or more elements, each element of the set having a different corresponding enlargement ratio, the telescopes or telemicroscopes together having a logarithmic progression of angular magnification. The set further includes a first telescope or telemicroscope having a lowest angular magnification value, a final telescope or telemicroscope having a highest angular magnification value, and one or more elements having in between angular magnification values, wherein the angular magnification increment between any two successive elements of the set is equal to $K(0.10)$ log, where K is an integer >0 or a fraction whose denominator is an integer >0.

In one or more embodiments, one or more telescopes or telemicroscopes of the set may be packaged and sold.

According to a fifth embodiment of the present disclosure, a set of electronic device magnifiers is provided. The set includes one or more electronic device magnifiers, each electronic device magnifier configured to provide a set of enlargement ratios that together have a logarithmic progression of enlargement ratio values. The set further includes a lowest enlargement ratio value, a highest enlargement ratio value, and one or more in between enlargement ratio values, wherein the log-increment between any two successive enlargement ratio values of the set is equal to K(0.10) log, where K is an integer >0 or a fraction whose denominator is an integer >0.

In one or more embodiments, one or more telescopes or telemicroscopes of the set may be packaged and sold.

According to a sixth embodiment of the present disclosure, a set of optical, telescopic, or electronic magnification devices is provided. The set includes one or more devices configured to provide non-rectilinear magnification to give the user a wider field of view and/or reduced contour interaction. The non-rectilinear magnification can be applied using 0.10 log 10 increments to tailor the amount of image formatting as desired. These devices maintain a logarithmic progression of magnification values. The set further includes a lowest magnification value, a highest magnification value, and one or more in between magnification values, wherein the log-increment between any two successive magnification values of the set is equal to K(0.10) log, where K is an integer >0 or a fraction whose denominator is an integer >0.

In one or more embodiments, one or more non-rectilinear magnifiers of the set may be packaged and sold (or be included as an image enhancement feature of an electronic magnifier).

BRIEF DESCRIPTION OF THE DRAWINGS

FIG. 1 illustrates specifications of an example set of handheld or spectacle lens magnifiers, according to one embodiment disclosed herein.

FIG. 2A illustrates specifications of an example set of stand magnifiers, according to one embodiment disclosed herein.

FIG. 2B is a plot of true enlargement ratio versus labeled power for the example set of stand magnifiers of FIG. 2A.

FIG. 3A illustrates an example set of magnifiers, according to one embodiment disclosed herein.

FIG. 3B presents a larger image of the example electronic magnifier of FIG. 3, for ease of viewing.

FIG. 3C illustrates examples of non-rectilinear magnification using the log MAG scale, according to various embodiments disclosed herein.

FIGS. 4A, 4B and 4C present comparisons of actual measured enlargement ratios with indicated power, for several lines of stand magnifiers currently marketed as professional-grade stand magnifiers.

FIG. 5A illustrates an example 10 diopter system clinical application example.

FIG. 5C illustrates an example 10 Diopter system from an electronic magnifier or telescopic device, according to one embodiment disclosed herein.

DETAILED DESCRIPTION

Figure 5B:
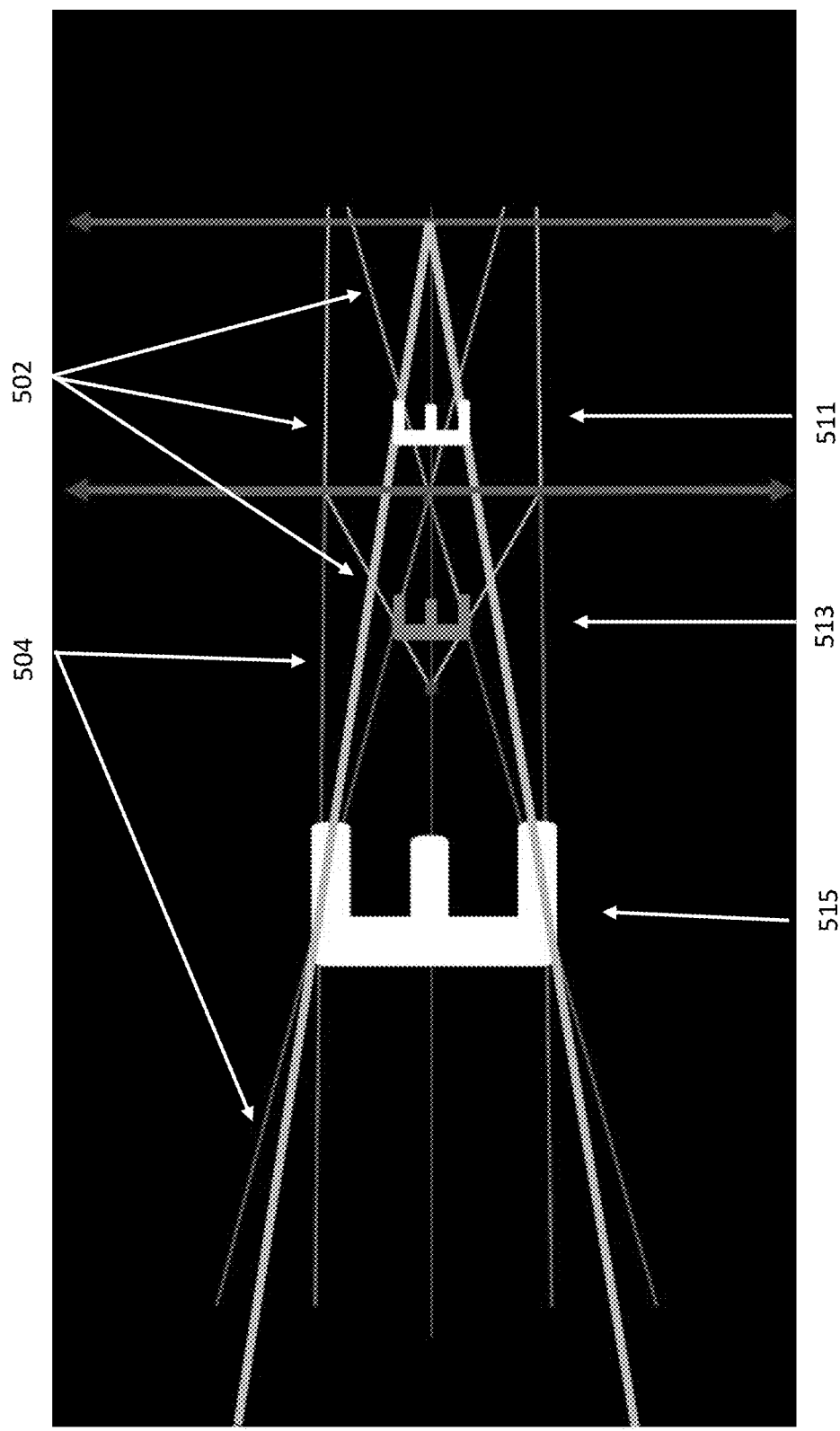
FIG. 5B illustrates an example 10 Diopter system optical stand magnifier, according to one embodiment disclosed herein.

In one or more embodiments, a set of magnifiers having a systematic progression of magnification powers from lowest to highest magnification is presented.

In one or more embodiments, such a set of magnifiers may be offered as a product line of spectacle and/or hand magnifiers. The product line includes a set of at least three magnifiers, each magnifier having a different corresponding diopter value, the magnifiers having a sequence of evenly incremented diopter values. The set includes a magnifier having a lowest value ($MAG_0$), a magnifier having a highest value ($MAG_N$), and one or more magnifiers having values between those of $MAG_0$ and $MAG_N$. In one or more embodiments, the diopter value increment between any two successive magnifiers of the set is equal to K(0.1) log, where K is an integer >0.

For clarity, a Diopter is a unit of measurement of the optical power of a lens, which is equal to the reciprocal of the focal length measured in meters. It is thus a unit of reciprocal length. For example, a 3 Diopter lens brings parallel rays of light to focus at ⅓ meter (33.33 cm). Similarly, a 10 Diopter lens brings parallel rays of light to focus at 1/10 meter (10 cm).

Additionally, as used herein, including in the claims, the term "enlargement ratio" refers to the size of a viewed magnified image of an object compared to the actual size of the object being magnified.

As an example to illustrate the ambiguities in conventionally available magnifiers, in the product line of a large international manufacturer of stand magnifiers, products that are labeled "4×" and "5×" have virtually the same enlargement ratio, as do those labeled as "10.75×" and "13×." Moreover, the magnifier labeled "8×" has an actual enlargement ratio about 14% less than that of the one labeled "7×". These facts are presented in FIG. 4B, described below. Furthermore, the "7×" product has an image distance measured at 48 cm. For clarity, the image distance is the distance from the stand magnifier lens to the virtual optical image viewed by the patient looking through the stand magnifier lens. This makes it impossible to achieve a perfectly clear image if the patient is wearing a spectacle add above +2.00 D, since adds stronger than this are in focus at a distance shorter than 48 cm away from the patient's eyes (many visually impaired patients wear a spectacle add of +2.50 D or stronger). It is also here noted that a +D value in the "add" portion of an eyeglass prescription is a correction for presbyopia.

Given these systemic ambiguities, low vision treatment is the only field of medical optical prescribing where the prescribing professional must either measure the devices for himself or herself, or depend on a third party to do so. Further, it is believed that only one of the large international manufacturers of hand and stand magnifiers makes technical information readily available to vision rehabilitation professionals for their products. The other manufacturers simply leave a prescribing professional in the dark. Thus, as noted above, a better set of magnification devices is needed.

Described below are example sets of magnifiers, in accordance with one or more embodiments. These sets of magnifiers generally fall into two types, namely hand held magnifiers, and stand magnifiers. In what follows, these are described one at a time.

In one or more embodiments, a set of handheld magnifiers may be provided. Specifications for such an exemplary set are illustrated in FIG. 1.

With reference to FIG. 1, an example set of spectacle and/or hand magnifiers is illustrated. As noted in the figure, objects of regard are observed from the focal point of magnifying lenses. The green lines and the enlarged letter "E" indicate angular size increase of print relative to viewing distance of first device in the series (arbitrarily for this example). Thus, stronger lenses allow for closer viewing, making print appear relatively larger.

The example set of magnifiers together includes a logarithmic progression of powers in diopters of equivalent power (EP) (as opposed to front or back vertex power). For example, as shown, the example set begins with a +5.0 D (log=0.7) magnifier, increases in 0.1 log steps, and ends with a 50 D (log (EP)=1.7) magnifier. In FIG. 1, for each Diopter of EP, the log of the EP is provided, as well as a diagram of proximal magnification.

In one or more embodiments, the set of magnifiers may be accurately labeled in diopters of equivalent power. It is noted that handheld magnifiers should not be labeled in "×" power, as the formulas for converting from D to × are arbitrary for D/4 and meaningless, especially with D/4+1. This is because the D/4 formula predicts the magnification compared to an arbitrary reference distance of 25 cm, but patients with low vision use a very wide variety of reading and working distances. Thus, comparing magnification to a viewing distance of 25 cm is neither helpful nor relevant for the vast majority of patients. The D/4+1 formula is an effort by manufacturers to imply that their magnifiers magnify more than they do for the arbitrary reference distance of 25 cm. Because manufacturers would not be able to sell many +4.00 D magnifiers that are labeled as "1×" (using the D/4 formula), using the D/4+1 formula allows them to market their +4.00 D magnifiers as "2×".

In one or more embodiments, the magnifiers may be provided with at least one LED for illumination. In some embodiments, at least two color temperatures of LED illumination in a set may be provided. These may be provided in different models, for example, one LED per model, or, for example, within the same model, there may be multiple LEDs. In one or more embodiments the LEDs may be replaceable.

In one or more embodiments, the set of magnifiers may be provided with better ergonomic features, so as to make them both more efficient as well as comfortable to use. For example, one or more of the following may be provided: comfortable grip, angled lens-to-handle connection for rectangular lens shapes, options for short or long lanyards for wrist or neck support for carrying, rechargeable batteries.

In one or more embodiments, a set of stand magnifiers may be provided. Such an exemplary set is illustrated in FIG. 2A. It is noted in connection with FIG. 2A that an original object placed inside the focal point of a lens results in a projected image that is enlarged according to log MAG standards with gradually increasing image distances. In one or more embodiments, these enlarged image progressions may also be generated using telescopic optics or electronic magnification. The illustrated magnified images must be viewed from some dioptric distance (e.g., 3D or 33 cm) in order to be converted to equivalent viewing power.

With reference to FIG. 2A, the example set of stand magnifiers has a logarithmic progression of powers of enlargement ratio. For example, the set may begin with a 2.0× (log=0.3) stand magnifier, and increase in 0.10 log steps up through a 16× (log=1.2). Continuing with reference to FIG. 2A, for each enlargement ratio, there is also shown its logarithm, the relevant image distance, and a diagram of transverse optical magnification. The entries in FIG. 2A thus progress in 0.10 log 10 steps, and thus the scale is proportional in the same units as visual acuity, lens power, or enlargement ratio.

FIG. 2B is a plot of true enlargement ratio ("ER") versus labeled power for the example stand magnifiers of FIG. 2A. As shown, there is an essentially perfect correspondence between true ER and the labeled power, thus making it easy to use such a set of stand magnifiers, as well as to be able to rely upon its accuracy, and the accuracy of stated incremental differences between magnifiers in the set.

In one or more embodiments, the set of stand magnifiers is accurately labeled with enlargement ratio, as well as image distance in centimeters. It is noted that labeling in D by itself is not helpful, as the height of the stand also affects the magnification.

In one or more embodiments, within the set, image distance increases incrementally along with enlargement ratio, as shown in FIG. 2A, and, in some embodiments, the image distance of a magnifier of the set is not greater than 33 cm, so that any magnifier of the set may be used by any patient or user with a spectacle add of +3.00 D or less.

In one or more embodiments, the set of magnifiers may be provided with better ergonomic features, so as to make them both more efficient as well as comfortable to use. For example, one or more of the following may be provided: comfortable grip, angled lens to reduce a user having to lean forward to achieve a nearly perpendicular view through the lens, rechargeable batteries, and options for at least two color temperatures of LED illumination, either in different models, or within the same model, which could include replaceable LEDs or more than one LED in the same device.

FIG. 3A illustrates various types of magnification devices, including both individual magnifiers as well as examples of sets of magnifiers. With reference thereto, FIG. 3A includes six rows, each depicting a different example. These are next described, one at a time.

Continuing with reference to FIG. 3A, a first row illustrates an example of a spectacle magnifier. A spectacle magnifier is worn by a user. The second row of FIG. 3A illustrates an example illuminated handheld magnifier, and the third row illustrates an example illuminated stand magnifier. The fourth and fifth rows of FIG. 3A present example magnifier sets. Thus, the fourth row depicts an example set that includes both illuminated handheld magnifiers (e.g., as shown in the second row) as well as illuminated stand magnifiers (e.g., as shown in the third row). The fifth row depicts an example set of telescopic magnifiers, which may be, for example, monocular, binocular, handheld, or spectacle mounted, in one or more embodiments. Finally, the sixth and last row of FIG. 3A depicts an example electronic magnifier.

FIG. 3B presents a larger image of the example electronic magnifier of FIG. 3A, for ease of viewing.

FIG. 3C illustrates several examples of non-rectilinear magnification using the log MAG scale, according to various embodiments disclosed herein. This feature is next described.

In one or more embodiments, a given image may be intentionally warped so as to squeeze more characters on the screen (or within a given lens window's field of view). This process is similar to what is done with anamorphic lenses to fit widescreen footage onto square frame film, which is usually indicated by an informational blurb that says "The following text has been modified from its original version. It has been formatted to fit this screen." In one or more embodiments, for example, this "formatting" could be done on the same log 10 magnification scale described herein. Thus, if an electronic device were used, it could ratchet from a square frame to 0.10 or 0.20 log steps more of magnification in one direction relative to the magnification in another direction. For example, there could be greater magnification in a vertical direction than in a horizontal direction, for example, or vice versa. It is noted that this could actually occur between any two directions, and may, for example, be user programmable, in whole or in part, depending upon the types of images that are being displayed. In this disclosure, such greater/lesser magnification in one direction relative to another direction (usually orthogonal, but not limited to be) is termed as "non-rectilinear", and may, for example, encompass fish eye or other types of image squeezing beyond bi-axial. In one or more embodiments, the non-rectilinear magnification may be applied in 0.10 log 10 proportional amounts. IN other embodiments, different increments may be used.

Thus, for example, alternatively, a series of magnifiers may be provided with a fixed 0.20 log 10 of non-rectilinear magnification, where each device is 0.10 log 10 stronger than the previous.

In one or more embodiments, for example, an electronic device that has an image enhancement mode may be provided where the user may toggle the amount of smearing of the image so as to reduce the amount of text scrolling necessary. In such examples, there is a trade-off between the amount of smearing tolerated and the quantity of text that can be displayed on the screen at a time.

Thus, in one or more embodiments, a set of optical, telescopic, or electronic magnification devices is provided. The set includes one or more devices configured to provide non-rectilinear magnification to give the user a wider field of view and/or reduced contour interaction. The non-rectilinear magnification can be applied using 0.10 log 10 increments to tailor the amount of image formatting as desired. These devices maintain a logarithmic progression of magnification values. The set further includes a lowest magnification value, a highest magnification value, and one or more in between magnification values, wherein the log-increment between any two successive magnification values of the set is equal to K(0.10) log, where K is an integer >0 or a fraction whose denominator is an integer >0.

In one or more embodiments, one or more non-rectilinear magnifiers of the set may be packaged and sold (or be included as an image enhancement feature of an electronic magnifier).

Illustrating this is the example shown in FIG. 3C. With reference thereto, in FIG. 3B there are four example displays of a magnified portion of text on an example electronic magnifier. While similar to the example shown in FIG. 3B, the three displays labelled "0.10", "0.20" and "0.30", are non-rectilinear magnification, where the text is always the same height, but has been smeared to fit more characters on the screen in the horizontal direction. Many other examples of non-rectilinear magnification are possible, it is understood, and all are within the scope of this disclosure.

In one or more embodiments, sets of magnifiers may be provided, where the magnifiers are presented in a predefined increment of the log of equivalent power or of enlargement ratio. For example, there may be a set of hand held magnifiers having equivalent powers selected from those shown in FIG. 1, which are incremented by 0.1 log, or by 0.2 log, for example, of equivalent power. Similarly, there may sets of any of the magnifier types illustrated in FIG. 3, and within each set the elements may be in a log MAG progression. In the case of electronic magnifiers, for example, in one or more embodiments, an electronic magnifier may be programmed to follow a log MAG progression. Thus, for example, as shown in the sixth row of FIG. 3, and as shown in the larger image of FIG. 3A, the electronic magnifier has a "+", or "increase magnification" button at the right side of the device. It also has a "−" or "decrease magnification" button just below it, which is obscured in the image by a user's right thumb. The example device may be, as noted, programmed to increase or decrease in a log MAG progression, such as, for example, by a 0.1 increment of the $\log_{10}(ER)$, as shown in FIG. 2A.

Similarly, for example, in some embodiments, a set of stand magnifiers may be provided, with, for example, powers of enlargement ratio selected from those shown in FIG. 2A, which are incremented by 0.1 log, or by 0.2 log, for example, of enlargement ratio. Or, for example, in some embodiments, a mixed set of both hand held and stand magnifiers may be provided, having any range of powers selected from those shown in FIGS. 1 and 2A, where the elements of each type of magnifier are incremented by some factor K of the log of their power, where K is an integer. For example, there may be a mixed set of (i) 11 hand held magnifiers having the powers shown in FIG. 1, and (ii) 10 stand magnifiers having the powers shown in FIG. 2, each magnifier labeled with its respective power and its log.

FIGS. 4A through 4C illustrate the ambiguities that pervade the field of low vision magnifiers. Each of FIGS. 4A, 4B and 4C present current offerings of sets of stand magnifiers from three example well known and prominent manufacturers. For each magnifier in the set, there is shown the labeled power, the actual measured ER, and a plot that compares the two values for each magnifier in the set. In each case there was significant deviation in actual ER from the stated or labeled × power. It is recalled here that, as shown above in FIG. 2B, in one or more embodiments the correspondence of labeled power to measured power is essentially perfect. It is noted that while FIGS. 4A through 4C plot the true ER versus the labeled power (×), ER is not the same as power. ER can be converted into equivalent power once the dioptric viewing distance is considered. Thus, 1D away is 1 meter viewing distance. 10D is 10 cm viewing distance. Looking at 2.0× of an object from 5D away is thus the same as looking at 5× of that same object from 2D away, as both equal 10D equivalent power (i.e., a 10 cm viewing distance).

At the bottom of each of FIGS. 4A through 4C there is a plot of true ER versus labeled power. In each plot, the labeled power is presented in a solid blue line, and the actual measured ER ("true ER") as a set of orange squares. Turning now to FIG. 4A, it is seen that in no case did the actual measured ER match the labeled power. In some cases, the measured power for a higher labeled power was actually lower than that of a nominally "lower" powered magnifier, such as, for example, for labeled power 10×, the actual ER, which is 6.4× was lower than that for labeled power 8×, which was 10.2×!

It is convenient to compare the logs of indicated power as shown in FIG. 4A with those shown in the example of FIG. 2A, discussed above. In order to do this, a viewing distance must be assumed to convert enlargement ratio to equivalent viewing power. For this purpose, a 3D (33 cm/~1 foot) viewing distance is convenient. Thus for the example line of magnifiers of FIG. 2A, ER×3D~equivalent power of the respective lens started with.

With reference to FIG. 4B, a similar deviation of actual ER from that which is stated is seen. At both ends of the provided range the values are less than or slightly above the indicated power, but in the middle of the range, for example for indicated powers of 7, 8 and 10.75×, the actual measured ER is much higher. Once again the actual progression of powers has some regression. Thus, for indicated powers of 10.75× to 13×, actual ER actually drops, from 12.8× to 12.5×, and for indicated powers 7× and 8×, the actual measured ER drops form 12.5× to 10.8×, which can only result in confusion to a user, unsatisfied with the 7× magnifier, trying to use a higher magnification.

Finally, with reference to FIG. 4C, a similar confusion prevails. In this example provider's offerings, the actual measured ER generally exceeds the labeled power. This is most egregious for magnifiers above an indicated power of 5×. Moreover, although offerings are provided for both 3.9× and 4×, the 3.9× is too low at 2.7×, but the 4.0× is much higher, at 4.7×. It is noted that offerings are provided by this example manufacturer for both 3.9× and 4.0× because the 3.9× has a square lens shape, and is intended to target the same patient who uses the 4× round magnifier but desires a larger lens viewing window.

As may be appreciated from FIGS. 4A, 4B and 4C, conventional offerings of sets of magnifiers are both inaccurate as labeled, confusing to users, and do not conform to any regular logarithmic increment between successive elements of the set.

FIGS. 5A through 5C, next described, each illustrate a clinical example of a 10 Diopter system in each of a spectacle or handheld, stand and electronic, or telescopic magnifier. These are respectively next described.

FIG. 5A illustrates a clinical application example. With reference thereto, the example is a 10 Diopter system with print equivalently scaled for three different viewing proximities. As shown, the two green lines 501 (with acute angle between them of approximately 30 degrees) diagram an angular image size requirement for comfortable reading of a typical print by an example patient with 20/100 visual acuity.

In FIG. 5A, the capital Letter E is initially viewed from 10 cm (i.e., 10 Diopters), and has been enlarged for two viewing proximities that are further away. At the 10 cm distance the E 503 is shown in white (at the far right of the figure), and at each of the two farther viewing distances, shown to the left of the white capital E, the letter E is shown in gray. These two distances are a first 503 at 32 cm (3.125 Diopters), and a second 505 (farther left) at 50 cm (2 Diopters) in order to maintain an equivalent viewing power (1×*10D)=10D. Thus, an enlargement ratio of 3.2 is used at 32 cm (3 Diopters) at 503 and an enlargement ratio of 5× is used at 50 cm (2 Diopters) at 505, to maintain an equivalent viewing power, where for all cases, the viewing power equals ER*Diopter Value, which is 10.

Similarly, FIG. 5B illustrates an example 10 Diopter system optical magnifier, according to one embodiment disclosed herein. As shown, an image of a large white capital letter "E" 515 located at a 3.125 diopter (32 cm) viewing distance has been generated by a log MAG stand magnifier with a 3.2× enlargement ratio. The generated "E" 515 is shown in white, while the original object used to generate this image, the smaller "E" 513, is shown in gray. Optical ray tracings in yellow 502 and orange 504 (to mark the direction of light travel) are diagrammed using two sets of principal light rays. These lines illustrate the physics of magnified image production by a convex lens. The log MAG lens is modeled as a simplified thin gray lens with outward facing arrow heads marked by a red focal point. For an object inside the focal point of the lens, light traveling from the top and bottom of the object proceeding towards the optical center of the lens will pass straight through without being deflected. Light rays traveling from the focal point through the top and bottom of the object will proceed parallel to the center line upon exiting the lens. The size and location of the enlarged image is derived by tracing the intersection of the two sets of principal rays. The original object is not visible to the observer since the light emerging from the optical magnifier follows the visual angle of the enlarged image (shown by the green lines). As also shown in FIG. 5B, this generated result has the same angular size as the original (i.e., "1×") letter 511 (shown at the far right of the figure, in white) as directly viewed from 10D (10 cm). This is because (1×*10D)=(3.2× *3.125D)=10D.

Finally, FIG. 5C illustrates an example 10 Diopter system using an electronic magnifier or telemicroscopic device, according to one embodiment disclosed herein. With reference thereto, as in FIG. 5B, the small white "E" 521 at the far right of the figure represents an object viewed at a distance 10 cm from the eye using 10 Diopters of add or accommodation. The two gray "E"s 523, 525 to the left of the small white E represent the same original object 523 and image 525 located at 32 cm, as described in FIG. 5B (515 in FIG. 5B), that was generated with the optical stand magnifier. Finally, the large white "E" 527 at the far left of the figure represents a 5× enlarged image (relative to the original print object) displayed on the screen of an electronic magnifier viewed from 50 cm (2 Diopters) from the eye.

Alternatively, the large white E 527 at the far left may also represent an image magnified by a 5× telescopic device with a 2 Diopter cap for viewing an object at 50 cm. It is noted that all of these scenarios result in the same angular size as the original letter directly viewed from 10D (10 cm) because (1×10 Diopters)=(3.2×3.125 Diopters)=(5×2 Diopters)=10 Diopters (10D).

It is noted that sets of magnifiers according to one or more embodiments offer numerous advantages over any magnifier, or set of magnifiers, now available. These advantages are next described.

In one or more embodiments, the magnifiers in an example set progress in rational logarithmic increments. It is here noted that a corollary of this occurred in visual acuity testing charts, which have been revolutionized over the last three decades by a log MAR (the log of the minimal angle of resolution) progression of optotype sizes. This has set new clinical standards and, if visual acuity is important to a given research project, publication without use of a log MAR chart is now nearly impossible. Eye care professionals understand logarithmic progression and its scientific merit.

By matching the magnifier power increments of 0.10 log to the same 0.10 log MAR increments that are used in modern visual acuity and reading performance charts, such as, for example, the MNRead and SK Read, in one or more embodiments, an example set of magnifiers may directly correlate to magnification prediction. Thus, for each line of visual acuity or critical print size reduction documented in a given patient's evaluation, one step of magnification increase would be required. This serves to simplify professional prescribing considerably.

It is even possible to directly align predicted equivalent viewing power with the visual acuity row on the eyechart (if a 2× functional magnification reserve is assumed). For clarity, 1M print=1 Diopter (1 meter) viewing distance for a 20/20 patient. A 2× reserve is a 2D viewing distance (½ a meter) for the same person, which is more comfortable as it only requires 20/40 acuity to view. As regards hand held magnifiers and visual acuity, if using a 2× reserve is desired (as is recommended in at least four clinical studies), a person with 20/100 vision would require a 10 D add or hand held magnifier used at its focal point to read 1.0M text (again, with a 2× reserve). One step worse is 20/125, which predicts a 12.5 D. Another step worse, 20/160, requires a 16 D lens, etc. Thus, the visual acuity denominator decimal point may be moved one space to the left to provide the predicted dioptric power, a very easy mathematical manipulation.

In one or more embodiments, prescribing is facilitated by working in the same log units for a modern visual acuity chart, 2× functional reserve, and dioptric power of the magnifier lenses. If a 2× functional reserve is assumed, patient's recommended equivalent dioptric power is always 0.3 log steps above their visual acuity, as the log(2)=0.30. Therefore, a patient with 20/100 visual acuity (log MAR 0.70) would be presented with a 10D (log MAG 1.0) lens. The prescriber could arrive at this lens working entirely in log units: 0.70 log visual acuity+0.30 log functional reserve=1.0 log lens power.

As regards stand magnifiers and reading performance, because total magnification is a function of both the magnifier and the patient's "add" (e.g., bifocal power in an older patient) or accommodation (e.g., focusing power of a younger patient), the situation is a little more complex. The total or "equivalent power" is the product of the stand magnifier's enlargement ratio and the dioptric power of the add or accommodation used by the patient. For example, a patient using a +3.00 D add and also using a stand magnifier with an ER of 4.0× will have an equivalent power of +12.00 D (3.00×4.0). The equivalent power needed to read normal sized 1.0M continuous text is the critical print size divided by the test distance in meters. It is here noted that critical print size, often evaluated with assessment tools such as the MNRead or SK Read, is the smallest passage of continuous text that a patient can read at his or her maximum reading speed and is the gold standard metric in low vision rehabilitation for prescribing magnification for reading. As an example of calculating equivalent power, if the critical print size is 2.5M and the patient was tested at 30 cm (0.30 meters) the required equivalent power is 2.5/0.3=+8.33 D. This number must now be divided by the add power or accommodation used to arrive at the predicted ER needed in a stand magnifier. These calculations take clinical time and are not known to some providers, and so are not frequently used despite strong evidence to their effectiveness. It is further complicated by the fact that currently available stand magnifiers available for professional prescribing are not available in these log progressions and are frequently not accurately labeled.

Accordingly, by designing a series of stand magnifiers in log progression that match the log steps used in standard visual acuity charts and continuous text reading assessment tools, the calculation is much easier. For example, if a patient wears a 2.50 D add and the critical print size is determined to be 2.0M at 40 cm, a stand magnifier with an enlargement ratio of 2.0× is predicted. If the patient will be wearing the same add power while using a stand magnifier as was used to determine the critical print size (as is often the case), the magnification needed from the stand magnifier to read normal sized, newspaper or magazine text is equal to the critical print size. A critical print size of 2.5M predicts a stand magnifier with an enlargement ratio of 2.5×, a critical print size of 3.2M predicts an enlargement ratio of 3.2×, etc. Thus, the critical print size equals the magnifier's predicted enlargement ratio Although a 2.50 D add is common, and a 40 cm test distance corresponds to that D value, as long as the test distance corresponds to the add power, the same relationship results. The log progression of ER and accurate labeling greatly simplifies the prescribing of these devices, as is clearly seen.

Using sets of magnifiers in accordance with various embodiments, dispensing professionals can prescribe with greater confidence and accuracy, given that actual technical specifications appear on the magnifiers. In this vein it is noted that early manufacturers who may choose to offer such sets of magnifiers commercially will likely gain immediate recognition, praise and gratitude from vision care professionals who have long been frustrated with the current system. In the inventors' opinion, such market praise and gratitude directly translates to increased sales.

Embodiments according to the present invention are particularly appealing to teachers of low vision rehabilitation, such as are on faculty in schools and colleges of optometry. By presenting the exemplary sets of magnifiers to their students as treatment options, such students would likely be inclined to utilize such sets after graduation.

The presentation of various embodiments according to the present invention in the professional marketplace would be highly educational to professionals, some of whom never learned how to prescribe on a scientific basis. Thus, use of magnifiers according to one or more embodiments would also elevate the level of patient care, improving independence for visually impaired individuals.

It is here noted that many patients with visual impairment are seniors, some of whom also have arthritis or tremors, making changing batteries difficult. Moreover, the need to change batteries and dispose of spent ones is now considered old fashioned and environmentally irresponsible. People today expect their portable electronic devices to be rechargeable, as provided in one or more embodiments.

More attention is now being devoted to the color temperature of illumination for visually impaired patients (LuxIQ, Stella lamps, etc.). Thus, in one or more embodiments, providing each element of a set of magnifiers, whether hand held or stand magnifiers, with LEDs of at least two different color temperatures allows the visually impaired patient to maximize performance by choosing the color temperature that best suits them.

The embodiments and examples set forth herein were presented in order to best explain the embodiments in accordance with the present technology and its particular application and to thereby enable those skilled in the art to make and use the disclosure. However, those skilled in the art will recognize that the foregoing description and examples have been presented for the purposes of illustration and example only. The description as set forth is not intended to be exhaustive or to limit the disclosure to the precise form disclosed.

In view of the foregoing, the scope of the present disclosure is determined by the claims that follow.

What is claimed is:

1. A method, comprising:
providing a set of stand magnifiers, the set including a sequence of evenly incremented enlargement ratio values, including:
a magnifier having a lowest value ($MAG_0$),
a magnifier having a highest value ($MAG_N$), and
one or more magnifiers having in between values, wherein the log-increment between any two successive magnifiers of the set is equal to K(0.1) log of enlargement ratio, where K is an integer >0 or a fraction whose denominator is an integer >0,
wherein at least one of:
the value of $MAG_0$ is +2.0×;
the value of $MAG_N$ is +16.0×; or
the lowest enlargement ratio of the set is 1.6×, the highest enlargement ratio of the set is 16.0×, and there are nine magnifiers with enlargement ratio values in between.

2. The method of claim 1, further comprising at least one of:
labelling the magnifiers of the set as to enlargement ratio;
labelling the magnifiers of the set as to log of enlargement ratio;

labelling the magnifiers of the set are labeled as to both enlargement ratio and log of enlargement ratio; or providing the magnifiers of the set are provided with a comfortable grip.

3. The method of claim 1, wherein at least one of:

one or more of the magnifiers of the set are provided with an LED for illumination;

one or more of the magnifiers of the set are provided with an LED for illumination and each provided LED may have one of a set of pre-defined color temperatures; or each magnifier of a subset of the set of magnifiers is provided with two LEDs for illumination, each LED having a different color temperature.

4. The method of claim 1, further comprising packaging one or more elements of the set for sale.

5. A set of stand magnifiers, made via the method of claim 1.

6. A method, comprising:

providing a set of telescopes or telemicroscopes, the set including:

a first telescope or telemicroscope with an enlargement ratio value of 1.6× (log=0.30);

a final telescope or telemicroscope with an enlargement ratio value of 16× (log=1.20); and one or more interim telescopes or telemicroscopes each having an enlargement ratio selected from the values of 2.5×, 3.2×, 4.0×, 5.0×, 6.3×, 8.0×, 10.0× and 12.5×.

7. The method of claim 6, further comprising at least one of:

labelling each element of the set with both an enlargement ratio and an image distance; or labelling each element of the set with both an enlargement ratio and an image distance and providing the image distance in centimeters.

8. The method of claim 6, wherein the image distance of each element of the set is 33 cm or less.

9. The method of claim 6, wherein there are eight interim telescopes or telemicroscopes have enlargement ratios of 2.5×, 3.2×, 4.0×, 5.0×, 6.3×, 8.0×, 10.0× and 12.5×.

10. The method of claim 6, further comprising packaging one or more elements of the set for sale.

11. A set of telescopes or telemicroscopes, made via the method of claim 6.

12. A set of stand magnifiers, having a sequence of evenly incremented enlargement ratio values, the set including:

a magnifier having a lowest value ($MAG_0$), a magnifier having a highest value ($MAG_N$), and one or more magnifiers having in between values, wherein the log-increment between any two successive magnifiers of the set is equal to K(0.1) log of enlargement ratio, where K is an integer >0 or a fraction whose denominator is an integer >0;

wherein at least one of:

the value of $MAG_0$ is +2.0×;

the value of $MAG_N$ is +16.0×; or the lowest enlargement ratio of the set is 1.6×, the highest enlargement ratio of the set is 16.0×, and there are nine magnifiers with enlargement ratio values in between.

13. The set of stand magnifiers of claim 12, wherein at least one of:

the magnifiers of the set are labelled as to enlargement ratio;

the magnifiers of the set are labelled with log of enlargement ratio; or the magnifiers of the set are labeled as to both enlargement ratio and log of enlargement ratio.

14. The set of stand magnifiers of claim 12, wherein the magnifiers of the set are provided with a comfortable grip.

15. The set of stand magnifiers of claim 12, wherein at least one of:

one or more of the magnifiers of the set are provided with an LED for illumination;

one or more of the magnifiers of the set are provided with an LED for illumination and each provided LED may have one of a set of pre-defined color temperatures; or each magnifier of a subset of the set of magnifiers is provided with two LEDs for illumination, each LED having a different color temperature.

16. A set of telescopes or telemicroscopes, the set including:

a first telescope or telemicroscope with an enlargement ratio value of 1.6X (log=0.30);

a final telescope or telemicroscope with an enlargement ratio value of 16X (log=1.20); and one or more interim telescopes or telemicroscopes each having an enlargement ratio selected from the values of 2.5X, 3.2X, 4.0X, 5.0X, 6.3X, 8.0X, 10.0X and 12.5X.

17. The set of telescopes or telemicroscopes of claim 16, wherein each element of the set is labelled with at least one of:

both an enlargement ratio and an image distance; or both an enlargement ratio and an image distance, wherein the image distance is provided in centimeters.

18. The set of telescopes or telemicroscopes of claim 16, wherein the image distance of each element of the set is 33 cm or less.

19. The set of telescopes or telemicroscopes of claim 16, wherein there are eight interim telescopes or telemicroscopes, having enlargement ratios of 2.5X, 3.2X, 4.0X, 5.0X, 6.3X, 8.0X, 10.0X and 12.5X, respectively.

20. The set of telescopes or telemicroscopes of claim 16, further comprising one or more elements of the set provided in a package for sale.

* * * * *